United States Patent [19]

Ito et al.

[11] Patent Number: 4,945,053

[45] Date of Patent: Jul. 31, 1990

[54] NOVEL ALKALINE CELLULASES AND A MICROORGANISM FOR PRODUCING THE SAME

[75] Inventors: Susumu Ito; Tomokazu Sato; Katsuya Ozaki; Shitsuw Shikata, all of Utsunomiya; Kikuhiko Okamoto, Koshigaya; Shigeo Inoue; Kenzo Koike, both of Utsunomiya; Yuichi Ota; Akira Takei, both of Hasaki, all of Japan

[73] Assignee: Kao Corporation, Tokyo, Japan

[21] Appl. No.: 110,774

[22] Filed: Oct. 21, 1987

[30] Foreign Application Priority Data

Oct. 28, 1986 [JP] Japan ................................ 61-257775
Oct. 28, 1986 [JP] Japan ................................ 61-257776
Oct. 28, 1986 [JP] Japan ................................ 61-257777
Oct. 28, 1986 [JP] Japan ................................ 61-257778

[51] Int. Cl.$^5$ .......................... C12N 9/42; C12R 1/07
[52] U.S. Cl. ............................. 435/209; 435/252.5; 435/832
[58] Field of Search ................. 435/209, 252.5, 832

[56] References Cited

U.S. PATENT DOCUMENTS 3,844,890 10/1974 Horikoshi et al. .................. 435/832

FOREIGN PATENT DOCUMENTS 271004 6/1988 European Pat. Off. .
273125 7/1988 European Pat. Off. .

OTHER PUBLICATIONS

Sippola et al., "Coproduction of Several Exoenzymes in Bacillus Subtilis," FEMS Microbiol. Lett., vol. 10, No. 4, pp. 303-306, 1981.

Chemical Abstracts, vol. 104, 1986, p. 312, abstract No. 64633g, Columbus, Ohio, US; F Fukumori et al.: "Purification and Properties of a Cellulase".

Chemical Abstracts, vol. 101, 1984, p. 334, abstract No. 87124u, Columbus, Ohio, US; K. Horikoshi et al.: "Cellulases of an Alkalophilic Bacillus Strain".

Biological Abstracts, No. 34060285, Philadelphia, Pa., US; J. H. Yu et al.: "Molecular Cloning of a CMCASE Gene From alkalophilic Sp. and Its".

*Primary Examiner*—Robert A. Wax
*Attorney, Agent, or Firm*—Oblon, Spivak, McClelland, Maier & Neustadt

[57] ABSTRACT

Novel alkaline cellulase K, CMCase I and CMCase II are obtained by isolation from a culture product of Bacillus sp KSM-635.

These enzymes stably work in a wide range including an alkaline side, and their activity is shown even at low temperatures. Further, they have a strong resistance to surface active agents, chelating agents and proteinases. Therefore, they can be effectively utilized not only as an additive for clothing detergents, but also as a biomass and in other fields.

8 Claims, 11 Drawing Sheets

NOVEL ALKALINE CELLULASES AND A MICROORGANISM FOR PRODUCING THE SAME

BACKGROUND OF THE INVENTION

1. Field of the Invention

This invention relates to a novel cellulase, a CMCase isolated from the cellulase, and a microorganism capable of producing the cellulase.

2. Discussion of the Background

The term cellulases refers to a complicated enzymatic system. This enzymatic system is a catalyst for the enzymatic reaction by which cellulose and similar polysaccharides are decomposed into glucose, cellobiose or celloligosaccharides.

The term cellulases is considered to be a general name for enzymes which are called, depending upon their mechanism of activity, $C_1$ enzyme, Cx enzyme and beta-glucosidase, or exo-beta-glucanase, endo-beta-glucanase, cellobiase and the like.

Cellulases have been studied mainly for the purpose of effectively utilizing biomass resources. For instance, the main source of cellulase supply has been fungi belonging to the genera *Trichoderma, Aspergillus, Acremonium,* and *Humicola*. However, cellulases deriving their origin from microorganisms including fungi involve a diversity of enzymes having differing working specificities and physiocochemical properties. The different enzymes which make up this enzymatic system have not yet been completely identified or studied.

Of these cellulases, those which have a high action on carboxymethyl cellulose (CMC) or Cx enzymatic action are generally called CMCases. In recent years, novel industrial utility for cellulases, including the CMCases, have been developed, particularly, as an additive for use in detergent compositions for clothing.

However, so far as cellulases produced by microorganism in nature and, particularly, the abovementioned cellulases originating from microorganism are concerned, they are, in most cases, so unstable that their activity is lost in an alkaline pH. These are so-called acidic and neutral cellulases (whose optimum working pH is in the range of 4 to 6). So-called alkaline cellulases which meet the requirement for detergent compositions for clothing, i.e. those which have a maximum activity and are resistant in an alkaline range, are very small in number.

For instance, with regard to alkaline cellulases which are usable in detergent compositions for clothing, there are only several known methods for producing alkaline cellulases originating from alkalophilic microorganisms. These methods include a method in which microorganisms belonging to the genus *Bacillus* are cultivated and cellulase A is collected from the medium (Japanese Patent Publication No. 50-28515). They also include a method in which alkalophilic bacteria belonging to the genus *Cellulomonas* are cultivated to produce alkaline cellulase 301-A (Japanese Patent Application Laid-open No. 58-224686), a method for producing CMCase by cultivation of alkalophilic *Bacillus* No. 1139 (Horikoshi et al, *J. Gen. Microbiol.*, Vol. 131, page 3339 (1985)), and a method of producing an alkaline cellulase using a strain belonging to the genus *Streptomyces* (Japanese Patent Application Laid-open No. 61-19483).

There is thus a strong demand and need for cellulases having an optimum working alkaline pH and possessing enzymatic activity making them suitable for use in detergents for clothing in an alkaline range.

SUMMARY OF THE INVENTION

Accordingly it is an object of this invention to provide a novel cellulase enzyme having an optimum working alkaline pH.

It is another object of this invention to provide a novel cellulase enzyme useful in detergents for washing clothes in an alkaline medium.

The present inventors have made intensive studies and have found, in nature, a microorganism capable of producing alkali cellulases which satisfy all of the above objects of this invention and other objects which will become apparent from the description of this invention given hereinbelow. They have now found that a microorganism collected from a sample of soil of Hagagun, Tochigi-ken, Japan and belonging to the genus *Bacillus* was able to produce novel alkaline cellulase K effective as an additive for detergent compositions for clothing. Moreover, it was also found that when the alkaline cellulase was further purified, novel CMCases I and II were obtained as main components.

Accordingly, another object of this invention is to provide a novel alkaline cellulase K enzyme having an alkaline optimum working pH.

Another object of the invention is to provide novel CMCase I and II enzymes.

A further object of the invention is to provide a microorganism capable of producing these novel enzymes and a method for producing alkaline cellulase K by cultivating the microorganism and collecting the resulting alkaline cellulase K from the culture product.

DETAILED DESCRIPTION OF THE INVENTION AND PREFERRED EMBODIMENTS

Figure 1:
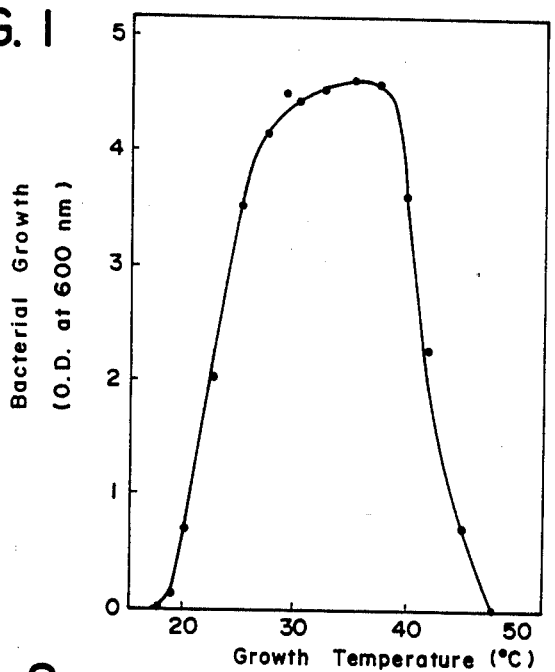
FIG. 1 is a graph showing a growth temperature range of *Bacillus* sp KSM-635.

The microorganism used for producing the novel enzymes according to the invention has the following mycological properties:

The media used for classification of strains are those media 1 to 24 and contain a suitable amount of a sterilized 1.0 wt% sodium carbonate ($Na_2CO_3$) solution unless otherwise indicated.

Compositions of Test Media for Classification (wt%)

Medium 1: Bacto peptone 0.5; meat extract 0.3; Bacto agar-agar 1.5

Medium 2: Bacto peptone 0.5; meat extract 0.3

Medium 3: Bacto peptone 0.5; meat extract 0.3; NaCl 7.0

Medium 4: Bacto peptone 0.5; meat extract 0.3; Bacto gelatin 20.0

Medium 5: Bacto litmus milk 10.5

Medium 6: Bacto peptone 0.5; meat extract 0.3; $KNO_3$ 0.1

Medium 7: Bacto peptone 0.7; glucose 0.5; NaCl 0.5

Medium 8: Bacto peptone 3.0; meat extract 0.3; sodium thiosulfate 0.005; cysteine hydrochloride 0.02; iron ammonium citrate 0.05; Bacto agar-agar 0.5

Medium 9: Bacto peptone 1.5; meat extract 0.4; lactose 1.0; sucrose 1.0; glucose 1.0; NaCl 0.5; sodium thiosulfate 0.008; sodium sulfite 0.04; ferrous sulfate 0.02; phenol red 0.002; Bacto agar-agar 1.5

Medium 10: Bacto peptone 1.5; yeast extract 0.5; soluble starch 2.0; $K_2HPO_4$ 0.1; Bacto agar-agar 1.5; $MgSO_4 \cdot 7H_2O$ 0.02

Medium 11: ammonium phosphate 0.1; KCl 0.02; yeast extract 0.05 $MgSO_4 \cdot 7H_2O$ 0.02; sugars 1.0 (sterilized separately through filtration)

Medium 12: potassium monohydrogen phosphate 0.1; ammonium dihydrogen phosphate 0.1; sodium citrate 0.2; $MgSO_4 \cdot 7H_2O$ 0.03; NaCl 0.05; Bromothymol Blue 0.0024; Bacto agar-agar 1.5

Medium 13: yeast extract 0.05; cysteine hydrochloride 0.01; sodium citrate 0.3; NaCl 0.5; sodium thiosulfate 0.008; iron ammonium citrate 0.04; glucose 0.02; potassium dihydrogen-phosphate 0.15; phenol red 0.0012; Bacto agar-agar 1.5

Medium 14: ammonium phosphate 0.1; potassium dihydrogenphosphate 0.05; sodium citrate 0.2; Bacto agar-agar 1.5; $MgSO_4 \cdot 7H_2O$ 0.02

Medium 15: yeast extract 0.05; $Na_2SO_4$ 0.1; $KH_2PO_4$ 0.1; glucose 1.0; inorganic nitrogen sources suitable amounts** * Sodium nitrate was added in 0.25%, sodium nitrite was in 0.2025%, ammonium chloride was in 0.158%, and ammonium phosphate was in 0.195% (each corresponding to 0.0412 N%).

Medium 16: yeast extract 0.05; $Na_2SO_4$ 0.1; $KH_2PO_4$ 0.1; glucose 1.0; inorganic nitrogen sources suitable amounts**; $CaCl_2 \cdot 2H_2O$ 0.05; $MnSO_4 \cdot 4-6H_2O$ 0.001; $FeSO_4 \cdot 7H_2O$ 0.001 (sterilized separately through filtration); $MgSO_4 \cdot 7H_2O$ 0.02 (sterilized separately through filtration)

** Sodium nitrate was added in an amount of 0.25%, sodium nitrite was in an amount of 0.2025%, ammonium chloride was added in an amount of 0.158%, and ammonium phosphate was in an amount of 0.195% (each corresponding to 0.0412 N%).

Medium 17: King A medium "Eiken" (available from Eiken Chem Co., Ltd.), indicated amounts Medium 18: King B medium "Eiken" (available from Eiken Chem. Co., Ltd.), indicated amounts Medium 19: potato dextrose agar-agar medium "Eiken" (Eiken Chem. Co., Ltd.), indicated amounts Medium 20: Bacto peptone 0.25; salt 0.25; yeast extract 0.25; mannitol 0.5; Bacto agar-agar 2.0

Medium 21: urea medium "Eiken" (available from Eiken Chem. Co., Ltd.), indicated amounts Medium 22: Bacto peptone 0.1; NaCl 0.5; $KH_2PO_4$ 0.2; yeast extract 0.05; glucose 0.1; urea 2.0; phenol red 0.001

Medium 23: Bacto peptone 0.5; yeast extract 0.5; $K_2HPO_4$ 0.1; glucose 1.0; $MgSO_4 \cdot 7H_2O$ 0.02

Medium 24: yeast extract 0.5; glucose 1.0; casein (Hammerstein, Merc Inc.) 0.5; $K_2HPO_4$ 0.1; $MgSO_4 \cdot 7H_2O$ 0.02; Bacto agar-agar 1.5

MYCOLOGICAL PROPERTIES

1. Results of Microscopic Observation

The Bacillus has a size of 0.5 to 1.2 $\mu m \times$ 1.5 to 4.0 $\mu m$ and makes an endospore (0.7 to 1.2 $\mu m \times$ 1.0 to 2.0 at one end of the bacillus body. Periflagela Motility: positive. Gram staining: positive.

2. The State of Growth in Various Media (1) Meat broth and agar-agar medium (medium 1)

The colony is circular in shape and has a flat surface. The colony is white or yellow in color and is semi-transparent and glossy.

(2) Meat broth liquid medium (medium 2) Growing and becoming turbid.

(3) 7% Salt meat broth liquid medium (medium 3) Growing and becoming turbid.

(4) Meat broth-gelatin stab culture (medium 4) Not growing.

(5) Litmus milk culture (medium 5)

Coagulation and peptonization of the milk: negative. Because of the alkalinity of the medium 5, no change in color of the litmus is recognized.

3. Physiological Properties (1) Reduction of nitrates and denitrification reaction Reduction of nitric acid: positive.

Denitrification: negative (medium 6).

(2) MR test (medium 7); Positive.

Because of the alkalinity of the medium, Methyl Red does not undergo any change, thus the judgement being impossible.

(3) VP test (medium 7) Positive.

(4) Formation of indole (medium 8)

Negative with respect to the reaction against an indole-producing test filter paper ("Nissan", made by Nissui Seiyaku K.K.) and also to the color change with Kovacs'indole reagent.

(5) Formation of hydrogen sulfide (medium 9) Negative.

(6) Hydrolysis of starch

A plate agar-agar medium, i.e. medium 10, which has been rendered acidic by the use of 4 N HCl is negative when determined by an ordinary detection method using the iodine reaction. In the liquid medium 11, formation of soluble starch is negative.

(7) Consumption of citric acid; Medium 11: positive.

Medium 12 (Koser's (Simons') citric acid/agar-agar plate medium): negative. A liquid medium which is obtained by eliminating agar-agar from the medium 12 and, instead, 0.05% of yeast extract is added, is positive.

Medium 13 (Christensen's agar-agar plate medium): positive, but no change with phenol red is observed because of the alkalinity.

Medium 14: negative (not growing). Positive with respect to a liquid medium which is obtained by eliminating agar-agar from the medium 14 and adding 0.05% of yeast extract.

(8) Utilization of inorganic nitrogen sources

Medium 15: negative to pseudopostive for all of nitric acid, nitrous acid and ammonia.

Medium 16: the present medium containing very small amounts of metal salts is positive with respect to nitric acid and nitrous acid. Ammonium chloride: pseudopositive. Ammonium phosphate: positive.

(9) Formation of dyes

Not growing in the King A medium (medium 17) and not possible to judge.

Light yellow (involving no fluorescence) in the King B medium (medium 18). Growing in a potato/dextrose/agar-agar medium (medium 19) and in a mannitol-/yeast extract/agar-agar medium (medium 20) but negative with respect to the formation of dyes.

(10) Urease

Medium 21: not growing. Negative when the formation ammonia with Nessler's reagent was confirmed after removal of phenol red from the medium 21 and cultivation of the present organism.

Medium 22 (Christensen's urea medium to which yeast extract is added): negative when the formation of ammonia with Nessler's reagent was confirmed after removal of phenol red from the medium and cultivation of the present organism. Negative when tested by changing the urea concentration in the medium 22 to 0.1, 0.2, 0.5, 1.0 and 2.0% on the presupposition of cytotoxin.

(11) Oxidase

"Positive" or "negative" is not clear.

(12) Catalase

Positive.

(13) Range of Growth (medium 23)

A temperature gradient incubator was used for shaking culture in an L-type test tube for 3 days. The growing temperature range was from 20° to 45° C. and an optimum growing temperature range was from 29° to 37° C. (FIG. 1).

Figure 2:
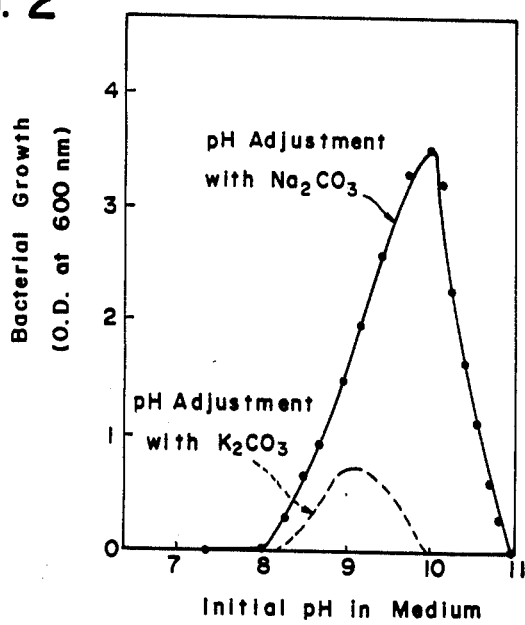
FIG. 2 is a graph showing a growth pH range.

In order to determine a pH range for growth, a test was conducted in which the concentration of $Na_2CO_3$ in medium 23 was changed to change the initial pH of the medium. As a result it was found that the growing pH range was from 8 to 11 and an optimum growing pH range was from 9.5 to 10.2 (FIG. 2). On the other hand, when the pH of the medium was controlled by the use of $K_2CO_3$, it was found that the amount of growth was very small and that optimum growing pH was about 9.

(14) Behavior on oxygen

Aerobic.

(15) Q-F test

Undergoes no change in color because of the alkalinity and growing only in an aerobic condition.

(16) Utility of Sugars (medium 11)

Utilizable carbon sources: D-ribose, L-arabinose, D-xylose, D-glucose, D-mannose, D-fructose, maltose, sucrose, trehalose, mannitol, inositol, and glycerin.

Non-utilizable carbon sources: D-galactose, lactose, sorbitol, starch, dextrin, and raffinose.

(17) Hydrolysis of casein (medium 24)

The microorganism was grown up in an agar-agar plate culture, into which 30% trichloroacetic acid was poured for judgement, revealing that no transparent zone were formed around the bacillus colonies, from which it was judged as negative.

(18) Requirement for nutrients

As is shown in Table 1, biotin (desthiobiotin) is essential for the growth.

TABLE 1

| Concentration of Vitamin (μg/ml) | | Degree of Growth of Bacillus sp KSM-635 |
|---|---|---|
| Biotin | Desthiobiotin | (Absorbance, 600 nm/6 days) |
| 0.001 | 0 | 4.6 |
| 0.01 | 0 | 4.6 |
| 0 | 0.001 | 4.3 |
| 0 | 0.01 | 4.4 |
| nil | | 0.0 |

Reference is made to Bergey's Mannual of Determinative Bacteriology, eighth edition, with respect to the above mycological properties, with the result that the present strain is considered as a spore-forming microorganism belonging to the genus Bacillus. However, since the present strain does not grow in a neutral pH but grows well only at a highly alkaline pH range, it can be provisionally determined that the microorganism is an alkalophilic microorganism, which has been recently reported by Horikoshi and Akiba in "Alkalophilic Microorganisms", Japan Scientific Society Press (Tokyo), 1982, and is distinguished from known bacilli growing in neutrality.

Because the mycological properties of the present strain do not coincide with those of known alkalophilic bacilli, the present strain has been determined to be a novel strain and has been named Bacillus sp KSM-635. It has been deposited as FERM BP-1485 at the Fermentation Research Institute of Japan (address: Fermentation Research Institute, Agency of Industrial Science and Technology, Ministry of International Trade and Industry, 1-3, Higashi 1-chome, Yatabe-Machi, Tsukuba-Gun, Ibaraki-ken 305, Japan).

For the production of alkaline cellulase K by the use of the above novel microorganism, Bacillus sp KSM-635, the strain of Bacillus sp KSM-635 or its variant is cultivated in a medium to produce alkaline cellulase K. This product is subjected to an ordinary enzyme purification method to isolate and purify it.

For the production by fermentation of alkaline cellulase K, a suitable medium is sterilized, such as by heating, and the strain of Bacillus sp KSM-635 (FERM BP-1485) is inoculated in the medium, followed by shaking or aeration spinner cultivation at 22° to 40° C., preferably from 26° to 37° C., for 1 to 4 days. Good results are obtained when the pH is adjusted to 8 to 11. Since the fermentation medium is alkaline in nature, it may sometimes foam, which can be controlled by the addition of a suitable amount of antifoam agent at suitable times.

The production of the alkaline cellulase K requires a suitable combination of nitrogen sources and carbon sources contained in a culture medium. These nutrient sources are not critical. For instance, nitrogen sources include inorganic sources such as ammonium nitrate, ammonium sulfate, ammonium chloride, ammonium phosphate, sodium nitrate and the like, and corn gluten meal, bean flour, corn steep liquor, casamino acid, yeast extract, Pharmamedia, sardine meal, meat extract, peptone, Hypro, Ajipower, corn soybean meal, coffee grounds, cotton seed oil meal, Cultivater, Amiflex, Ajipron, Zest, Ajix, and the like.

Examples of the carbon sources include plant fibers such as chaff, bran, filter paper, ordinary papers, sawdust and the like, and waste molasses, invert sugar, CMC, Avicel, cellulosic cotton, xylan, pectin and the like. Further utilizable carbon sources include, for example, ribose, arabionse, xylose, glucose, mannose, fructose, maltose, sucrose, trehalose, mannitol, inositol, glycerin and the like, and organic acids such as acetic acid, citric acid and the like.

Any media using combinations of these nitrogen and carbon sources may be used and the nutrient sources should not be limited to any specific ones.

Aside from these ingredients, phosphoric acid and inorganic salts such as of $Mg^{2+}$, $Ca^{2+}$, $Mn^{2+}$, $Zn^{2+}$, $Co^{2+}$, $Na^+$, $K^+$ and the like, and, if necessary, inorganic and organic trace nutrient sources may be added to the medium.

The alkaline cellulase K may be obtained from the thus obtained culture product according to any known techniques of collection and purification of ordinary enzymes as will be particularly described in examples appearing hereinafter.

For instance, the culture product may be subjected to centrifugal separation or ultrafiltration to separate the bacillus cells. The resultant culture broth is the subjected to ordinary isolation methods including, for example, salting-out, isoelectric precipitation, solvent precipitation (using methanol, ethanol, isopropanol or the like), thereby separating the protein as a precipitate. Alternatively, ultrafiltration (e.g. Diaflow Membrane YC, available from Amicon Co., Ltd.) may be used for concentration to obtain alkaline cellulase K.

After precipitation in ammonium sulfate (30 to 70% saturated fraction) for the salting-out method or 75% ethanol for the solvent precipitation method, the enzyme may be filtered, centrifugally separated or desalted to obtain a freeze-dried powder. The desalting may be effected by an ordinary procedure such as dialysis or gel filtration using Sephadex G-25 or the like. Moreover, the purification of the enzyme is possible by a suitable combination of, for example, a hydroxy apatite chromatography, an ion exchange chromatography using DEAE-Sephadex or DEAE-cellulose and a molecular sieve gel chromatography using Sephadex or Bio-gel.

The resultant alkaline cellulase K of the invention have the following physical and chemical properties.

Activity

The present enzyme has Cx enzymatic activity, acting on CMC. However, it also acts on phosphoric acid-swollen cellulose and possesses such specific activity as that of an enzyme acting on crystalline cellulose (cellulosic cotton) or Avicel, which is cellulose having high crystallinity (i.e. Avicelase), and the activity of a $C_1$ enzyme the typical activity of which is filterpaper-degrading activity (FPDase), and a beta-glucosidase activity on cellobiose and cellooligosaccharide. In addition, the enzyme slightly acts on the artificial substrate PNPC to liberate p-nitrophenol.

(2) Substrate Specificity

The alkaline cellulase K has no degradation activity on xylan, amylose, dextrin, pectin, inulin and cardolan. The Avicelase and FPDase activities are about 0.3% of the CMCase activity. The degradation activity on the artificial substrate of p-nitrophenyl cellobioside (PNPC) was about 1.5 to 1.8% of the CMCase activity (Table 2).

TABLE 2

| Action of Enzyme | Specific Activity (units/g of enzyme) |
| --- | --- |
| β- Glucosidase | 0.7 |
| PNPCase* | 5.2 |
| CMCase | 298 |
| FPDase | 1.2 |
| Avicelase | 1.1 |

*PNPC degrading activity

(3) Working pH and Optimum Working pH

Figure 3:
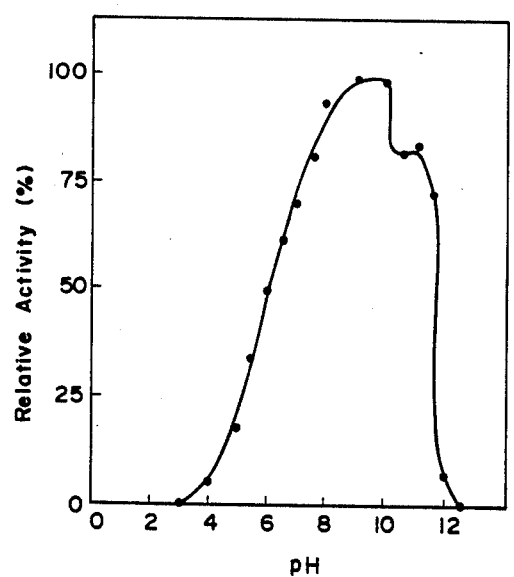
FIG. 3 is a graph showing a working pH range of CMCase of alkaline cellulase K.

The working pH of the present enzyme is from 4 to 12 and the optimum working pH is approximately from 9 to 10. At about a pH of 10.5, there appears a shoulder (FIG. 3).

(4) pH Stability

Figure 4:
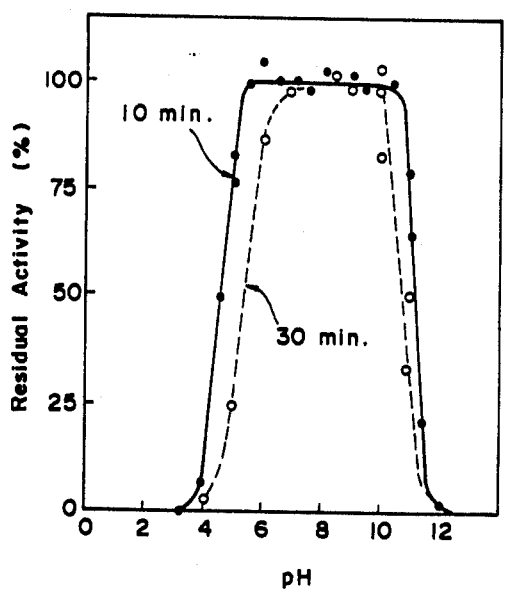
FIG. 4 is a graph showing pH stability.

Stable pH values, which are determined by allowing to stand in buffer solutions of different pHs at 40° C. for 10 minutes and 30 minutes, are, respectively, from 4.5 to 10.5 and 6.8 to 10 (FIG. 4). When allowed to stand at 5° C., the pH is 4 to 11 and the enzyme is stable for at least one month.

(5) Working Temperature Range and Working Optimum Temperature

Figure 5:
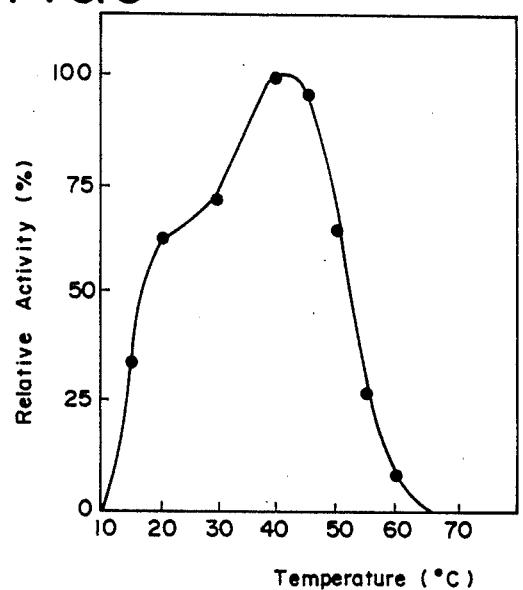
FIG. 5 is a graph showing a working temperature range of CMCase of alkaline cellulase K.

The present enzyme works over a wide temperature range of from 10° C. to 65° C. When the reaction is effected in a glycine buffer solution (pH 9) for 20 minutes, the working optimum temperature is found to be about 35 to 45° C., preferably about 40° C. (FIG. 5).

(6) Thermal Stability

Figure 6:
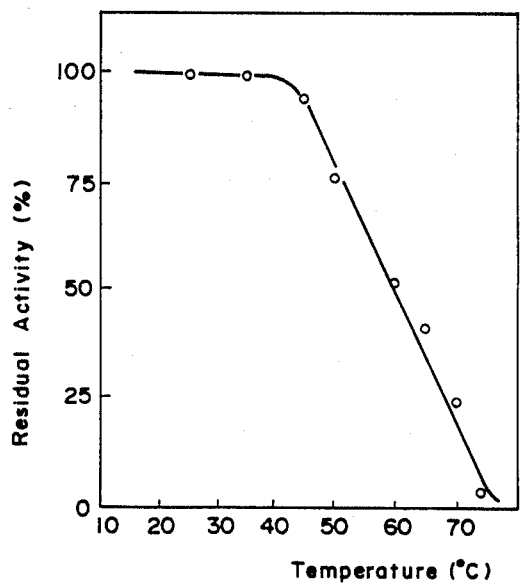
FIG. 6 is a graph showing thermal stability.

When thermally treated in a glycine buffer solution (pH 9) at different temperatures for 20 minutes, the present enzyme is not inactivated at all at about 40° C., and has a residual activity of about 50% at 60° C. and about 25% at 70° C. (FIG. 6).

(7) Measuring Methods of Enzymatic Activities and Proteins (i) CMCase activity An enzyme solution (0.1 ml) was added to a substrate solution composed of 0.2 ml of CMC (2.5%), 0.1 ml of a 0.5M glycine buffer solution (pH 9.0) and 0.1 ml of deionized water, followed by reaction at 40° C. for 20 minutes. After completion of the reaction, reducing sugar was quantitatively determined by the 3,5-dinitrosalicylic acid (DNS) method.

More specifically, 1 ml of a DNS reagent was added to 0.5 ml of the reaction solution and heated at 100° C. for 5 minutes for color development, followed by cooling and dilution with 4.5 ml of deionized water. This was subjected to colorimetry at an absorbance of 535 nm. The enzyme titer determined as one unit is an amount of the enzyme which is capable of producing reducing sugar corresponding to 1 $\mu$mol of glucose in one minute under the above-described conditions.

(ii) Decomposition Activity of PNPC

A suitable amount of CMCase was combined at 3° C., with 1.0 ml of a reaction solution containing 100 $\mu$mol of a phosphate buffer solution (pH 7.0) and 0.1 $\mu$mol of PNPC (Sigma Co., Ltd.), after which 0.3 ml of 1 M Na₂CO₃ and 1.7 ml of deionized water were added in this order, followed by subjecting the resultant free p-nitrophenol to colorimetry at 400 nm. The amount of the enzyme capable of liberating 1 μmol of free p-nitrophenol in one minute under the above conditions was determined as one unit.

(iii) Avicelase and RPDase activities

A reaction solution (2 ml) for measurement of the CMCase activity was provided, in which there was used, instead of the CMC substrate, 20 mg of Avicel (Merk Inc.) or a bulk piece of a filter paper having a width of 0.5 cm and a length of 5 cm (filter paper for determination of cellulase activity, Toyo No. 51-Specific), thereby determining Avicelase and FPDase activities. An amount of the enzyme capable of liberating 1 μmol of reducing sugar, calculated as glucose, in one minute under the above conditions was determined as one unit.

(iv) The quantitative determination of proteins was effected by the use of a Bio Rad Protein Assay Kit (Bio Lad Co., Ltd.) and bovine serum albumin was used for calculation as a standard protein.

(8) Influence of Chelating Agents

The resistance of the enzyme for detergents towards chelating agents in a builder used as a reaction composition is the most important factor. Alkaline cellulase K was pretreated with EDTA (0.5 mM), EGTA (0.5 mM), NTA (0.5 mM), sodium tripolyphosphate (STPP, 50 mg/ml) and zeolite (5 mg/ml) to determine a residual activity, but no influence was noticeable.

(9) Influence of Proteinases

Proteinases function to improve the detergency of detergent compositions. Accordingly, it is a matter of course to further improve the detergency by adding cellulases to proteinase-containing detergents. For this purpose, it is necessary to satisfy the requirement that cellulases for detergents are not hydrolyzed by proteinase and can maintain their activity. Alkaline cellulase K has a good resistance to actually employed proteinases for detergents (e.g. API-21, Maxatase, Alkalase and the like) and ordinary proteinases (e.g. pronase) (Table 3).

TABLE 3

| Added Proteinase | Concentration (wt %) | Relative Residual Activity (%)* |
|---|---|---|
| API-21 | 0.002 | 98 |
| (Showa Denko) | 0.02 | 100 |
|  | 0.2 | 114 |
| Maxatase | 0.002 | 113 |
| (Gist) | 0.02 | 99 |
|  | 0.2 | 99 |
| Alkalase | 0.002 | 110 |
| (Novo) | 0.02 | 108 |
|  | 0.2 | 99 |
| Pronase | 0.002 | 99 |
| (Sigma) | 0.02 | 98 |
|  | 0.2 | 102 |

*Treated with the respective proteinases at 15° C. for 12 hours. The activity of an enzyme preparation not treated was taken as 100% and the activity of the respective treated preparations was indicated as an index to the non-treated preparation.

(10) Influence of Metals

Divalent metal ions ($Hg^{2+}$, $Cu^{2+}$ and the like), at a suitable concentration give an inhibition effect. A slight degree of inhibition is experienced by means of monoiodoacetic acid and p-chloromercuribenzoate.

(11) Influence of Surface Active Agents

Alkaline cellulase K suffers little inhibition of activity by means of various surface active agents such as, for example, LAS, AS, ES, AOS, alpha-SFE, SAS, polyoxyethylene secondary alkyl ethers, fatty acid salts (sodium salts), and dimethyldialkylammonium chloride

(12) Molecular Weight (Gel Chromatography Using Sephadex G100)

Figure 7:
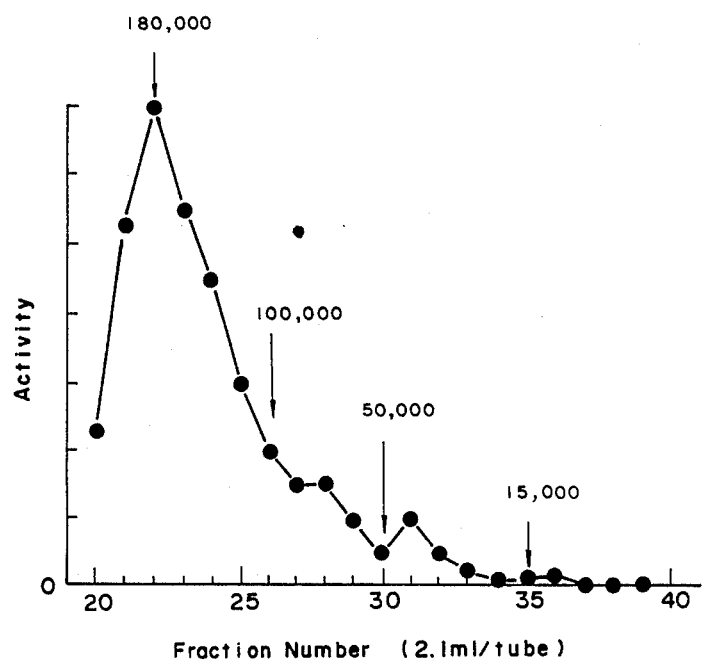
FIG. 7 is a graph showing the relation between elution fraction and activity in gel chromatography.

Having a maximum peak at 180,000±10,000 (FIG. 7).

The alkaline cellulase K of the invention as compared with known cellulases has the following properties:

The present alkaline cellulase has an optimum pH in a high pH range and is thus clearly distinguishable from cellulases, which have an optimum pH in an acidic range, of molds or germs belonging to the genera *Trichoderma, Penicillium, Asperqillus* ("Cellulases" by Kazutoshi Nishizawa, Tokyo Nankodo, 1974), *Acremonium* (Japanese Patent Publication No. 59-166081), *Humicola* (Japanese Patent Publication No. 61-16316) and the like.

When compared with the alkaline cellulase disclosed in Japanese Patent Publication No. 50-28515, the present alkaline cellulase has a molecular weight having a maximum peak at 180,000±10,000. On the other hand, known cellulases have a molecular weight of 15,000 to 30,000. The cellulase of *Bacillus* No. 1139 had a molecular weight of 92,000. Moreover, other physical and chemical properties are different from those of these known cellulases. Thus, the present cellulase is clearly distinguishable from these cellulases.

For obtaining CMCase I and CMCase II from alkaline cellulase K, the alkaline cellulase K is purified by means of a preparative high performance liquid chromatography, a hydroxy apatite chromatography and a DEAE-Toyopearl chromatography and the like, thereby isolating the respective constituents. CMCase I and CMCase II have different molecular weights and electrically charging properties slightly. For instance, they can be separated from each other by elution using a linear concentration gradient of NaCl in the DEAE-Toyopearl chromatography.

The thus obtained CMCase I and CMCase II have the following properties.

CMCase I

(1) Activity

The present enzyme has Cx enzymatic activity, acting on CMC. The enzyme has also acts on phosphoric acid-swollen cellulose and has such activity specificities as exhibiting the activity of an enzyme (Avicelase) acting on crystalline cellulose (cellulosic cotton) and Avicel which is a high crystallinity, and activity of a $C_1$ enzyme such as a filter paper degrading activity (FPDase) and a beta-glucosidase activity of acting on cellobiose and cellooligosaccharides. Furthermore, it slightly acts on PNPC which is an artificial substrate to liberate p-nitrophenol.

(2) Substrate Specificity

The main activity of the present enzyme is the CMCase activity and has about 0.3%, based on the main activity, of Avicelase and FPDase activities (Cl activity). The artificial PNPC substrate degrading activity is about 1.5 to 1.8% (Table 4). On the other hand, it has not any degrading activity on xylan, amylose, dextrin, pectin, inulin and curdlan.

TABLE 4

| Substrate Reacted | Enzymatic Activity (specific activity, units/mg of protein) of CMCase I |
|---|---|
| CMC | 6.56 |
| Filter Paper | 0.020 |
| Avicel | 0.019 |
| Cellobiose | 0.010 |
| PNPC | 0.099 |

(3) Working pH and Optimum Working pH

Figure 8:
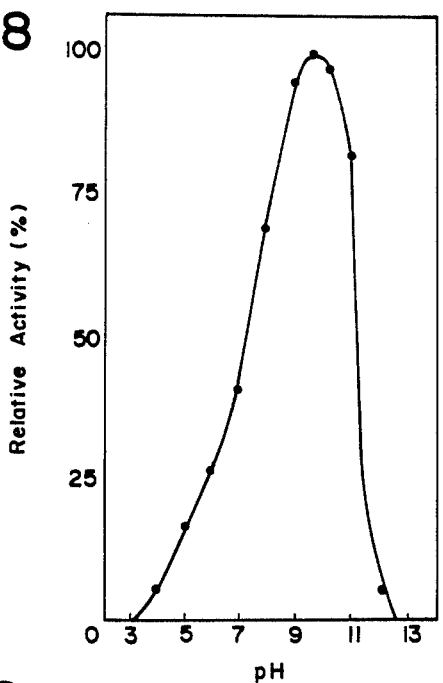
FIG. 8 is a graph showing the relation between pH at which CMCase I is reacted and relative activity.

The working pH of the present enzyme is from 3 to 12.5 and the optimum working pH is from 6 to 11.5 (FIG. 8). The pH at which the working is the highest is about 9.5.

The working pH range with respect to PNPC is from 4 to 11 and the optimum pH is about 6 to 8, preferably 7.

(4) pH Stability

Figure 9:
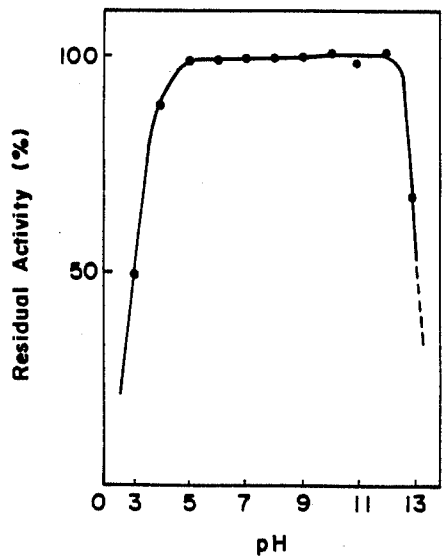
FIG. 9 is a graph showing the relation between pH at which CMCase I is treated and residual activity.

Stable pH values were determined by allowing the present enzyme to stand at different pH values at 30° C. for 1 hour and measuring a residual activity. As a result, the enzyme was very stable at a pH of from 5 to 12 and was not inactivated (FIG. 9).

(5) Measuring Enzymatic Activities and Protein

The CMCase activity, PNPC degrading activity, Avicelase and FPDase activity, and the content of proteins were measured in the same method as with the alkaline cellulase K.

(6) Working Temperature Range and Optimum Working Temperature

Figure 10:
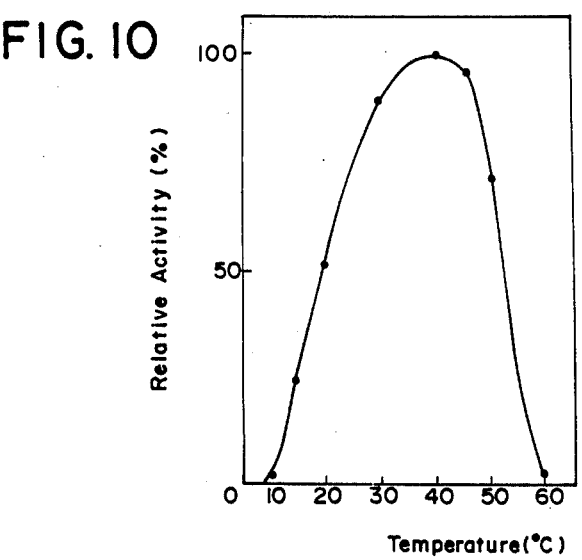
FIG. 10 is a graph showing the relation between reaction temperature (pH 9.0) of CMCase I and relative activity.
Figure 11:
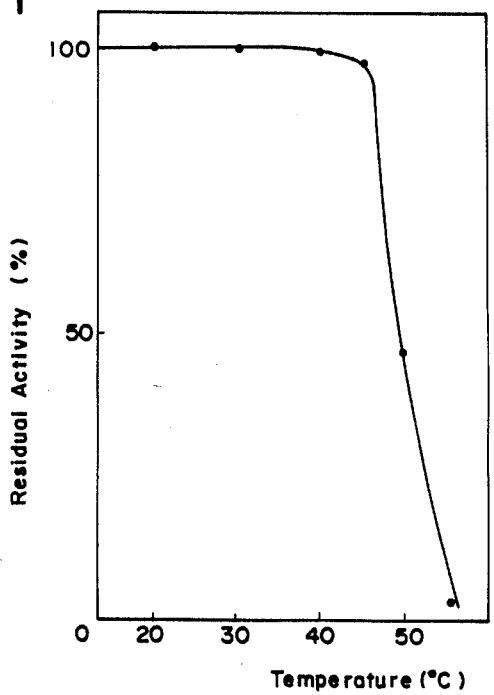
FIG. 11 is a graph showing the relation between treating temperature of CMCase I (pH 9.0) and residual activity.

The working temperature range of CMCase I is in the range of from 10° to 60° C. The preferable temperature range is from 22° to 53° C. The optimum working temperature of the present enzyme is about 40° C. The present enzyme has a good resistance at low temperature and has about 50% of the activity at a low temperature of 20° C.(FIG. 10).

(7) Thermal Stability

When thermally treated at 50° C. for 30 minutes, the enzyme has residual activity of about 50% (in glycine buffer solution: pH 9.0).

(8) Influence of Metals

Metals and ions give influences on the physicochemical properties, particularly a viscosity, of CMC. It will be apparent that when the activity of the enzymatic components of the present invention is measured using a CMC substrate, the factors of the reaction kinetics of the alkaline cellulose K are not correctly reflected.

Accordingly, on the basis of the indication that the CMCase I has the decomposition activity on PNPC, influences of metals on the enzymatic activity were determined. It was found that $Zn^{2+}$, $Co^{2+}$, $Ni^{2+}$, $Cu^{2+}$ and $Hg^{2+}$ inhibited the activity of the CMCase I. On the other hand, $Mn^{2+}$ and $Ba^{2+}$ promoted the activity slightly.

(9) Influence of Chelating Agents

When CMC was used as a substrate, CMCase I suffered no inhibition with EDTA, EGTA, NTA, STPP and zeolite.

(10) Influence of Sugars

Similar to (8), PNPC was used as a substrate for the CMCase I to determine the influences of various sugars. Cellobiose inhibited both enzymatic components and thus exhibited the mode of product inhibition, but other disaccharides, e.g. lactose and maltose, gave no influence. The activity was not inhibited with monosaccharides including glucosamine, N-acetylglucosamine, ribose, arabinose, sorbose, xylose, fructose, galactose, glucose, and their derivatives such as 3-0-methyl-beta-D-glucose, alpha-methyl-beta-D-glucose, alpha-methyl-D-glucoside, alpha-methyl-beta-mannoside and 2-deoxyglucose, and other saccharides such as rhamnose.

(11) Influence of Salt Concentration

A phosphate buffer solution, a bicine-Na buffer solution and a tris-HCl were used and salt (0 to 250 mM) was used as an ion-strength adjusting agent. The decomposition activity of PNPC was used as an index to determine an effect of the ion strength on the CMCase I. As a result, it was found that the ion strength had no relation to the enzymatic activity with respect to the promotion or inhibition.

(12) Influence of Surface Active Agents

The activity was rarely inhibited by means of LAS, AS, ES, AOS, alpha-SFE, SAS, polyoxyethylene secondary alkyl ethers, fatty acid salts (sodium salts), dimethyldialkylammonium chloride, and taurocholic acid.

(13) Molecular Weight

The molecular weight determined by gel chromatography (Toyopearl 55S, available from Toyo Soda Co., Ltd.) was 145,000+10,000.

(14) UV Absorption Spectrum

Figure 12:
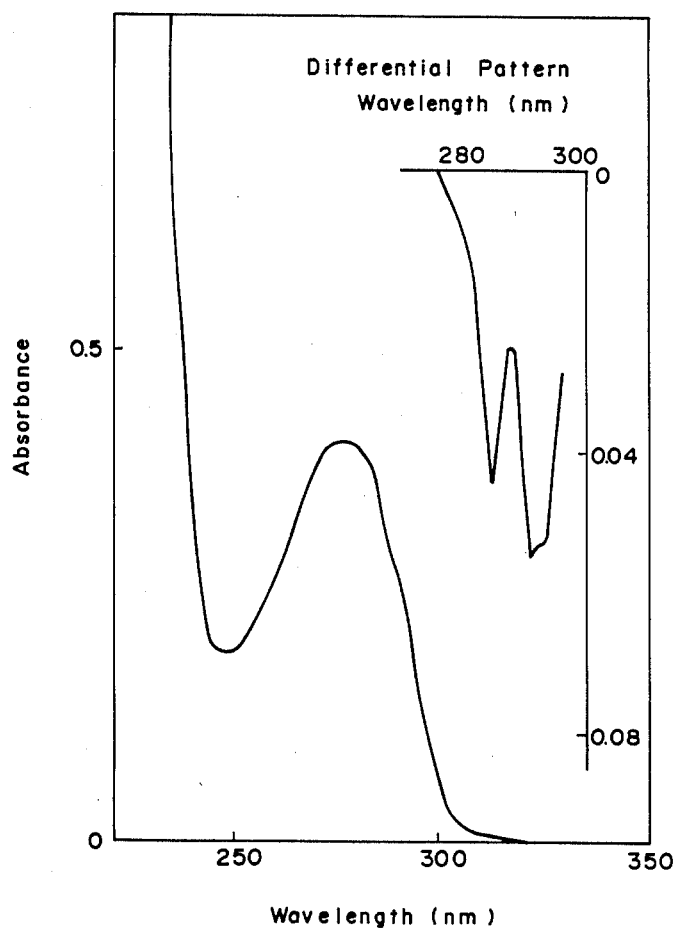
FIG. 12 is a UV absorption spectrum of CMCase I of the invention.

The present enzyme was dissolved in a bicine-sodium buffer solution and subjected to measurement of a UV absorption spectrum, revealing that it had a maximum absorption at about 280 nm with the existence of a shoulder absorption at 290 nm being found by checking a differential absorption spectrum (FIG. 12).

(15) Detection of Sugars

The purified enzyme protein was subjected to a color development test using a phenol/sulfuric acid method, with the result that a maximum absorption appeared at 480 nm. This result means that the present enzyme contains a sugar. The sugar was detected by gas chromatography using an Alditol/acetic acid method, indicating that (N-acetyl)glucosamine was contained as a sugar. The present enzyme had a content of the sugar of from 1.3 to 4.0 wt%.

(16) Resistance to Proteinases

Proteinases for detergents, e.g. API (showa Denko), Maxatase (Gist Co., Ltd.) and Alkalase (Nobo Co., Ltd.) (0.0002 to 0.1 wt%) were used in coexistence with the present enzyme and the residual activity of the preparations pre-incubated at 15° C. for 12 hours was measured. Inactivation was not recognized. Thus, the present enzyme was found to have a strong resistance to the proteinases (Table 5).

TABLE 5

| Added Proteinase | Concentration (wt %) | Relative Residual Activity (%) of CMCase I |
|---|---|---|
| Reference (no addition) | — | 100 |
| API-21 | 0.1 | 99 |
| (Showa Denko) | 0.01 | 112 |
| Maxatase | 0.1 | 102 |
| (Gist) | 0.01 | 108 |
| Alkalase | 0.1 | 111 |
| (Novo) | 0.01 | 116 |

CMCase II

(1) Activity

The present enzyme has Cx enzymatic activity, acting on CMC. The enzyme has also acts on phosphoric acid-swollen cellulose and has such activity specificities as exhibiting the activity of an enzyme (Avicelase) acting on crystalline cellulose (cellulosic cotton) and Avicel which is a high crystallinity, and activity of a $C_1$ enzyme such as FPDase and a beta-glucosidase activity on cellobiose and cellooligosaccharides. Furthermore, it slightly acts on PNPC which is an artificial substrate to liberate p-nitrophenol.

(2) Substrate Specificity

The main activity of the present enzyme is the CMCase activity and has about 0.3%, based on the main activity, of Avicelase and FPDase activities ($C_1$ activity). The artificial substrate PNPC degrading activity is about 1.5 to 2.0% (Table 6). Oh the other hand, it has not any degrading activity on xylan, amylose, dextrin, pectin, inulin and curdlan.

TABLE 6

| Substrate Reacted | Enzyme Activity (specific activity, units/mg of protein) of CMCase II |
|---|---|
| CMC | 7.06 |
| Filter Paper | 0.022 |
| Avicel | 0.020 |
| Cellobiose | 0.010 |
| PNPC | 0.140 |

(3) Working pH and Optimum Working pH

Figure 13:
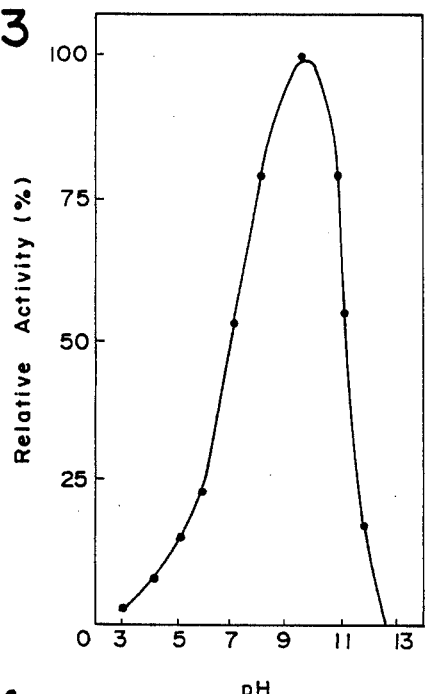
FIG. 13 is a graph showing the relation between reaction pH for CMCase II and relative activity.

The working pH of the present enzyme is from 3 to 12 and the optimum working pH is from 6 to 11.5 (FIG. 13). The pH at which the working is the highest is about 9.5.

The working pH range of the present enzyme with respect to PNPC is from 4 to 11 and the optimum pH is about 7.

(4) pH Stability

Figure 14:
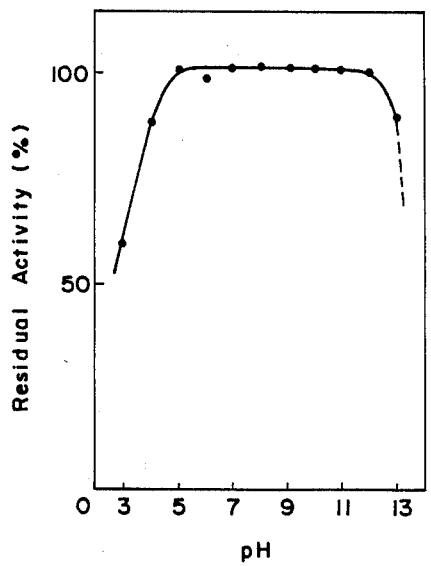
FIG. 14 is a graph showing the relation between treating pH of CMCase II and residual activity.

Stable pH values were determined by allowing the present enzyme to stand at different pH values at 30° C. for 1 hour and measuring a residual activity. As a result, the enzyme was very stable at a pH of from 5 to 12 and was not deactivated (FIG. 14).

(5) Measuring Enzymatic Activities and Proteins

The CMCase activity, PNPC degrading activity, Avicelase and FPDase activity, and the content of proteins were measured in the same manner as with the alkaline cellulase K.

(6) Working Temperature Range and Optimum Working Temperature

Figure 15:
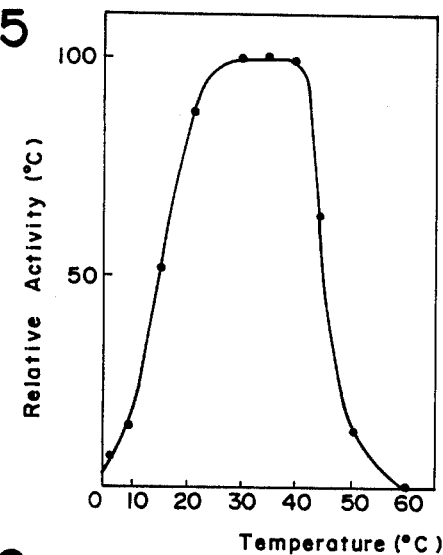
FIG. 15 is a graph showing the relation between reaction temperature of CMCase II (pH 9.0) and relative activity.

The working temperature range of CMCase II is in the range of from 5° to 58° C. The preferable temperature range is from 14° to 45° C. The optimum working temperature of the present enzyme is 30° to 40° C. At 15° C., the present enzyme has an activity of about 50% of the case of 30° to 40° C. where the maximum activity is shown (FIG. 15).

(7) Thermal Stability

Figure 16:
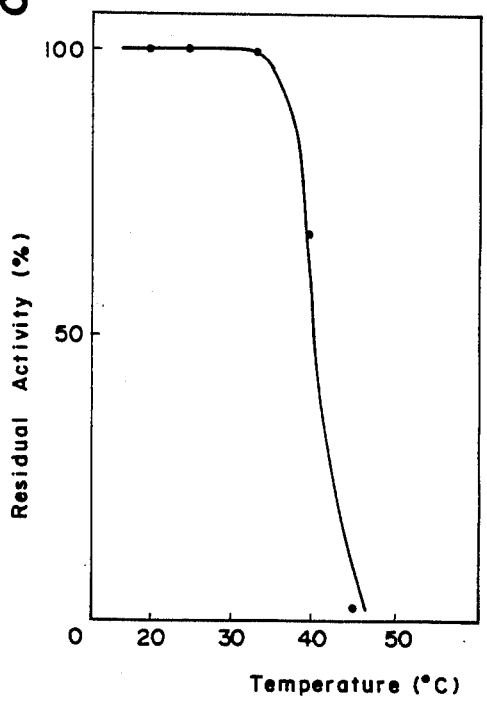
FIG. 16 is a graph showing the relation between treating temperature for CMCase II (pH 9.0) and residual activity.

When thermally treated at 40° C. for 30 minutes, the enzyme has a residual activity of about 75% (in glycine buffer solution: pH 9.0) (FIG. 16).

(8) Influence of Metals

Metals and ions give influences on the physicochemical properties, particularly a viscosity, of CMC. It will be apparent that when the activity of the enzymatic components of the present invention is measured using a CMC substrate, the factors of the reaction kinetics of the alkaline cellulase K are not correctly reflected. Accordingly, on the basis of the indication that the CMCase II has the decomposition activity on PNPC, influences of metals on the enzymatic activity were determined. It was found that $Zn^{2+}$, $Co^{2+}$, $Ni^{2+}$, $Cu^{2+}$, $Hg^{2+}$ and $Ca^{2+}$ inhibited the activity. On the other hand, $Mg^{2+}$, $Mn^{2+}$, $Ca^{2+}$, $Ba^{2+}$, $Fe^{2+}$, $Li+$, $K+$, and $Na+$ promoted enzyme activity to 1.1 to 2.4 times the original activity.

(9) Influence of Chelating Agents

When CMC was used as a substrate, the present enzyme suffered no inhibition with EDTA, EGTA, NTA, STPP or zeolites.

(10) Influence of Sugars

Similar to (8), PNPC was used as a substrate for the CMCase II to determine the influences of various sugars. Cellobiose inhibited both enzymatic components and thus exhibited the mode of product inhibition, but other disaccharides, e.g. lactose and maltose, gave no influence. The activity was not inhibited by monosaccharides including glucosamine, N-acetylglucosamine, ribose, arabinose, sorbose, xylose, fructose, galactose, glucose, and their derivatives such as 3-0-methyl-beta-D-glucose, alpha-methyl-beta-D-glucose, alpha-methyl-D-glucoside, alpha-methyl-beta-mannoside and 2-deoxyglucose, and other saccharides such as rhamnose.

(11) Influence of Salt Concentration

A phosphate buffer solution, a bicine-Na buffer solution and a tris-HCl were used and NaCl (0 to 250 mM) was used as an ion-strength adjusting agent. The decomposition activity of PNPC was used as an index to determine an effect of the ion strength on the CMCase II. As a result, it was found that the ion strength had no effect enzymatic activity with respect to the promotion or inhibition.

(12) Influence of Surface Active Agents

The activity was rarely inhibited by means of LAS, AS, ES, AOS, alpha-SFE, SAS, polyoxyethylene secondary alkyl ethers, fatty acid salts (sodium salts), dimethyldialkylammonium chloride, and taurocholic acid.

(13) Molecular Weight

The molecular weight determined by gel chromatography (Toyopearl 55S, available from Toyo Soda Co., Ltd.) was 170,000±20,000.

(14) UV Absorption Spectrum

Figure 17:
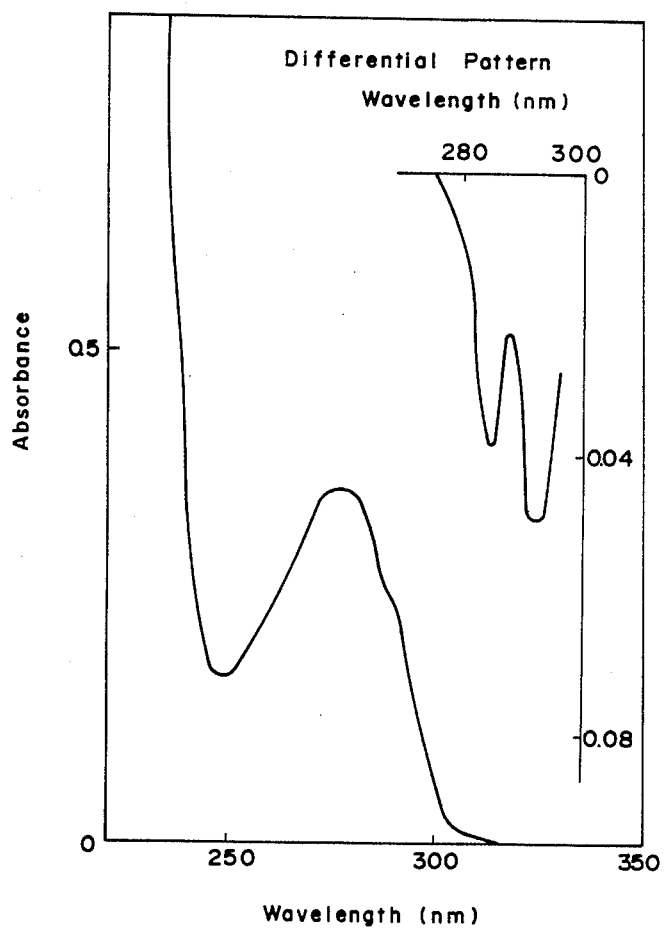
FIG. 17 is a UV absorption spectrum of CMCase II.

The present enzyme was dissolved in a bicine-sodium buffer solution and subjected to measurement of a UV absorption spectrum, revealing that it had a maximum absorption at about 280 nm with the existence of a shoulder absorption at 290 nm being found by checking a differential absorption spectrum (FIG. 17).

(15) Detection of Sugars

The purified enzyme protein was subjected to a color development test using a phenol/sulfuric acid method, with the result that a maximum absorption appeared at 480 nm. This result revealed that the present enzyme contains a sugar. The sugar was detected by gas chromatography using an Aldeytol/acetic acid method, indicating that (N-acetyl)glucosamine was contained as a sugar. The present enzyme had a sugar content of from 1.3 to 4.0 wt%.

(16) Resistance to Proteinases

Proteinases for detergents, e.g. API (Showa Denko), Maxatase (Gist Co., Ltd.) and Alkalase (Novo Co., Ltd.) (0.0002 to 0.1 wt%) were used in coexistence with the present enzyme and the residual activity of the preparations pre-incubated at 15° C. for 12 hours was measured. Inactivation was not recognized. Thus, the present enzyme was found to have a strong resistance to the proteinases (Table 7).

TABLE 7

| Added Proteinase | Concentration (wt %) | Relative Residual Activity (%) of CMCase II |
| --- | --- | --- |
| Reference (no addition) | — | 100 |
| API-21 | 0.1 | 102 |
| (Showa Denko) | 0.01 | 115 |
| Maxatase | 0.1 | 100 |
| (Gist) | 0.01 | 102 |
| Alkalase | 0.1 | 104 |
| (Novo) | 0.01 | 108 |

A comparison in properties between CMCases I and II and those of a known cellulase is as follows.

The present enzymes have an optimum pH in a high pH range and are thus clearly distinguishable from cellulases, which have an optimum pH in an acidic range, of molds or germs belonging to the genera *Trichoderma, Penicillium, Aspergillus* ("Cellulases" by Kazutoshi Nishizawa, Tokyo Nankodo, 1974), Acremonium (Japanese Patent Publication No. 59-166081), Humicola (Japanese Patent Publication No. 61-16316) and the like.

When compared with the cellulase disclosed in Japanese Patent Publication No. 50-28515 and the cellulase reported in *J. Gen. Microbiol.*, Vol. 131, page 3339 (1985), it will be found that CMCase I has a molecular weight of 145,000±10,000 and CMCase II has a molecular weight of 170,000±20,000, whereas the alkali cellulase of Japanese Patent Publication No. 50-28515 has a molecular weight of 15,000 to 30,000 and the molecular weight of *Bacillus* No. 1139 is 92,000. Moreover, the enzymes of the present invention apparently differ from these known cellulases in various reaction kinetic properties and the existence of the sugar therein.

The alkaline cellulase K and CMCases I and II obtained according to the invention are specific enzymes which exhibit stable activity over a wide range including the alkaline pHs.

For instance, the alkaline cellulase K has, at a pH of 11, a relative activity of about 75 to 80% based on the activity at the optimum pH. Although the optimum pH is at a strongly alkaline, good activity is shown at strongly acidic pH of about 4 or lower.

Likewise, CMCase I has a relative activity of about 75 to 80% at a pH of 11 based on the activity at an optimum pH and exhibits an activity even at a pH of about 3.5. CMCase II has a relative activity of about 70% at a pH of 11, based on the activity at an optimum pH and exhibits activity at a pH of about 3.

As will be apparent from the above, the alkaline cellulase K and the CMCases I and II of the present invention are enzyme groups which shown good activity at the most strongly alkaline side among hitherto known alkaline cellulases.

Moreover, these enzymes have the features that they are active even at low temperatures and that they have a strong resistance to surface active agents, chelating agents and proteinases. Accordingly, the alkaline cellulase K and CMCases I and II of the invention can be effectively utilized not only as an additive for clothing detergents, but also as a biomass and in other fields.

Other features of this invention will become apparent in the course of the following descriptions of exemplary embodiments which are given for illustration of the invention and are not intended to be limiting thereof.

EXAMPLE 1

A soil sample collected at Ichikai-machi, Hagagun, Tochigi-ken, Japan was suspended in a sterilized saline solution and thermally treated at 80° C. for 30 minutes. The thermally treated solution was suitably diluted and spread plated on a plate (composed of 1% of a meat extract (Oxoid Co., Ltd.), 1% of Bacto peptone (Difco Co., Ltd.), 1% of NaCl, 0.1% of $KH_2PO_4$, 0.5% of $Na_2CO_3$ (separately sterilized) and 1.5% of Bacto agaragar), followed by cultivation at 30° C. for 3 days, thereby forming colonies. Tranplantation on a 2% CMCcontaining plate as above according to a replica method was effected to again form colonies, followed by pouring a Congo Red dye solution to obtain colonies whose periphery was transparent. The thus obtained colonies were collected from the plate and high titer CMC-ase-producing bacilli were screened.

By the above procedure, *Bacillus* sp KSM-635 (FERM P-8872) of the invention was isolated.

EXAMPLE 2

The strain of *Bacillus* sp KSM-635 (FERM P8872) was aerobic cultivated in a liquid medium consisting of 1.5% of meat extract, 0.5% of yeast extract, 1% of CMC, 0.1% of $KH_2PO_4$ and 0.75% of $Na_2CO_3$ at 34° C. for 2 days. 3 liters of cooled ethanol (−10° C.) were gradually added to 1 liter of a supernatant liquid of the culture product to cause proteins to precipitate. The precipitate was dissolved in a minimum amount of sterilized deionized water and neutralized with diluted acetic acid, followed by dialysis with running water for 15 hours and freeze-drying to obtain 8.2 g of alkaline cellulase K. The thus obtained cellulase K had the following enzymatic activities shown in Table 8.

TABLE 8

| Kind of Enzyme | Specific Activity (units/g of enzyme powder) |
| --- | --- |
| β-Glucsidase | 0.6 |
| PNPCase* | 7 |
| CMCase | 325 |
| FPDase | 1.2 |
| Avicelase | 1.1 |

*PNPC degrading activity

EXAMPLE 3

A Hundred ml of a medium (pH 8.4 to 8.6) containing 1% of CMC, 2% of polypeptone, 0.1% of $KH_2PO_4$, 0.1% of yeast extract and 0.75% of $Na_2CO_3$ was placed in a 500 ml Erlenmeyer flask and sterilized by a usual manner, followed by inoculation of the strain of *Bacillus* sp KSM-635 (FERM P-8872) and shaking culture at 30° C. for 4 days. After completion of the culture, the bacillus cells were centrifugally removed and the resultant supernatant liquid was subjected to measurement of the CMCase activity. The activity was found to be 3,100 units/liter. This supernatant liquid was treated in the same manner as in Example 2 to obtain 9.2 g of alkaline cellulase K.

EXAMPLE 4

The strain of *Bacillus* sp KSM-635 (FERM P8872) was inoculated in a medium of Example 2 in which 1.5 % of meat extract was added instead of Bacto peptone, followed by shaking culture at 30° C. for 3 days. After the culture, a centrifugally separated supernatant liquid was subjected to measurement of the CMCase activity. As a result, the activity was found to be 3,200 units/liter.

EXAMPLE 5

One liter of the supernatant liquid obtained in Example 4 was purified according to the following procedure to obtain CMCases I and II. The purification was conducted by (1) treatment with streptomycin, (2) fractionation with ammonium sulfate (30 to 75% saturated precipitation fraction), (3) a preparative high performance liquid chromatography (e.g. SW 3000 G column (Toyo Soda Co., Ltd.)), (4) DEAE-Toyopearl (Toyo Soda Co., Ltd.) chromatography, (5) hydroxy apatite (Seikagaku Ind. Co., Ltd.) chromatography, and (6) DEAE-Toyopearl chromatography. At the sixth stage of the purification, when elution by a NaCl linear concentration gradient (from 0.25 M NaCl to 0.35 M NaCl) was effected, CMCase I and CMCase II were eluted according to the order of the elution speed to obtain 24 mg of CMCase I and 15 mg of CMCase II. The thus obtained CMCases I and II were subjected to electrophoresis according to the Davis method (Davis D. J., *Ann. N.Y. Acad. Sci.*, Vol. 121, page 404 (1964)), followed by dyeing with Coomassie Brilliant Blue. As a result, it was found that a single band was obtained for the respective enzymes.

EXAMPLE 6

Figure 18:
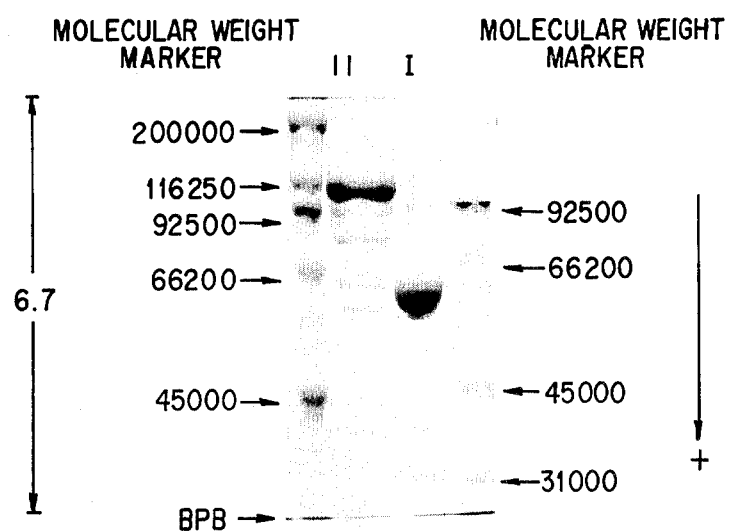
FIG. 18 is a view showing the results of sodium dodecylsulfate electrophoresis of CMCases I and II of the invention.

The CMCases I and II obtained Example 5 were subjected to electrophoresis using sodium dodecylsulfate according to a conventional procedure. The results are shown in FIG. 18. From the results, it was found that the CMCases I and II were association products of different molecule species having a lowest molecular weight of 30,000±2,000 and a highest molecular weight of 120,000±15,000. The CMCases I and II are assumed to be associated products of enzyme proteins which are strongly associated by some physical and chemical interactions and have a lowest molecular weight of 30,000±2,000. However, how the protein is associated is not known at present. It is considered that the main protein species of the CMCase I has a molecular weight of from 55,000 to 65,000 and the CMCase II has a molecular weight of from 95,000 to 120,000. Accordingly, the products obtained in this example are merely an example of the results of the sodiumdodecylsulfate electrphoresis and should not be construed as limiting exact subunit structures of the CMCases I and II.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A substantially pure alkaline cellulase K having the following set of physical and chemical properties:
    (1) activity:
       (1a) having Cx enzymatic activity, being capable of acting on carboxymethyl cellulose, (1b) weak $C_1$ enzymatic activity, and (1c) weak beta-glucoxidase activity;
    (2) specificity on substrates:
       being capable of acting on carboxymethyl cellulose (CMC), crystalline cellulose, microcystalline cellulose, cellobiose, and p-nitrophenyl cellobioside (PNPC);
    (3) working pH and optimum pH:
       having a working pH in the range of 4 to 12;
    (4) stable pH:
       being stable at pH values of 4.5 to 10.5 and 6.8 to 10 when allowed to stand at 40° C. for 10 minutes and 30 minutes, respectively;
    (5) working temperature range and optimum working temperature: having a working temperature range of from 10 to 65° C. with an optimum temperature being recognized at about 40° C.
    (6) influence of chelating agents:
       having activity unimpeded by ethylenediamine tetraacetic acid (EDTA), ethyleneglycol-bis-(β-aminoethylether) N,N,N',N"-tetraacetic acid (EGTA), N,N-bis(carboxylmethyl)glycine (nitrilotriacetic acid) (NTA), sodium tripolyphosphate (STPP) or a zeolite;
    (7) influence of surface active agents:
       capable of undergoing little activity inhibition by sodium linear alkylbenzenesulfonates (LAS), sodium alkylsulfates (AS), sodium polyoxyethylene alkylsulfates (ES, sodium alphaolefinsulfonates (AOS), sodium alpha-sulfonated aliphatic acid esters (alpha-SFE), sodium alkylsulfonates (SAS), polyoxyethylene secondary alkyl ethers, fatty acid salts (sodium salts), or dimethyldialkylammonium chloride;
    (8) influence of proteinases:
       being resist to proteinases;
    (9) molecular weight (determined by gel chromatography):
       having a maximum peak at 180,000±10,000.

2. The alkaline cellulase K of claim 1, said alkaline cellulase K being isolated from a culture product of *Bacillus* sp KSM-635.

3. A method for producing an alkaline cellulase K which comprises cultivating *Bacillus* species KSM-635, and collecting alkaline cellulase K from the resulting culture product.

4. A substantially pure CMCase I having the following physicochemcial properties:
  (1) activity:
    having Cx enzymatic activity, weak $C_1$ enzymatic activity and weak beta-glucosidase activity;
  (2) specificity on substrates:
    acting on carboxymethyl cellulose (CMC), crystalline cellulose, microcrystalline cellulose, cellobiose, and p-nitrophenyl cellobioside (PNPC);
  (3) working pH and optimum pH:
    having a working pH in the range of 3 to 12.5 and an optimum pH in the range of 6 to 11.5;
  (4) stable pH:
    not inactivated at a pH of 5 to 12 when allowed to stand at 30° C. for 1 hour;
  (5) working temperature and optimum working temperature:
    having a working temperature range of from 10 to 60° C. with a optimum temperature at 22 to 53° C.;
  (6) influence of chelating agents:
    having an activity unimpeded by ethylenediamine tetraacetic acid, ethyleneglycol-bis-(beta-aminoethylether)-N,N,N',N''-tetraacetic acid, N,N-bis(carboxymethyl)glycine (nitrilotriacetic acid), sodium tripolyphospate or a zeolite;
  (7) influence of surface active agents:
    undergoing little inhibition of activity by sodium linear alkylbenzenesulfonates, sodium alkylsulfates, sodium polyoxyethylene aldylsulfates, sodium alpha-olefin sulfonates, sodium alpha-sulfonated aliphatic acid esters, sodium alkylsulfonates, polyoxyethylene secondary alkyl ethers, fatty acid salts (sodium salts), dimethyldialkylammonium chloride, and taurocholic acid;
  (8) resistant to proteinase:
    having a strong resistance to proteinases;
  (9) molecular weight as determined by gel chromatography:
    having a molecular weight of 145,000±10,000;
  (10) UV absorption spectrum:
    having a maximum absorption at 280 nm and a shoulder absorption at 290 nm.

5. The CMCase I of claim 4, said CMCase I being isolated from a culture product of *Bacillus* sp KSM-635.

6. A substantially pure CMCase II having the following physical and chemical properties:
  (1) activity:
    having Cx enzymatic activity, weak $C_1$ enzymatic activity, and weak beta-glycosidase activity;
  (2) substrates specificity:
    acting on carboxymethyl cellulose (CMC), crystalline cellulose, microcrystalline cellulose, cellobiose and p-nitropenyl cellobioside (PNPC);
  (3) working pH and optimum pH:
    having a working pH in the range of 3 to 12.5 and an optimum pH in the range of 6 to 11.5;
  (4) pH stability:
    not in activated at a pH of 5 to 12 when allowed to stand at 30° for 1 hour;
  (5) working temperature and optimum working temperature:
    working in a temperature range of from 5 to 58° C. with an optimum temperature being at 14 to 45° C;
  (6) influence of chelating agents:
    having an activity unimpeded by ethylenediamine tetraacetic acid, ethyleneglycol-bis-(beta-aminoethylether)-N,N,N',N''-tetraacetic acid, N,N-bis(carboxymethyl)glycine (nitrilotriacetic acid), sodium tripolyphospate and zeolite;
  (7) influence of surface active agents:
    undergoing little inhibition of activity by sodium linear alkylbenzenesulfonates, sodium alkylsulfates, sodium polyoxyethylene alkylsulfates, sodium alpha-olefin sulfonates, sodium alpha-sulfonated aliphatic acid esters, sodium alkylsulfonates, polyoxyethylene secondary alkyl ethers, fatty acid salts (sodium salts), dimethyldialkylammonium chloride;
  (8) resistance to proteinases:
    having a strong resistance to proteinases;
  (9) molecular weight as determined by gel chromatography;
    having a molecular weight of 170,000±20,000;
  (10) UV absorption spection:
    having a maximum absorption at 280 nm and a shoulder absorption at 290 nm.

7. The CMCase II of claim 6, said CMCase being isolated from a culture product of *Bacillus* sp KSM 635.

8. A biologically pure strain of bacteria *Bacillis* species KSM-635 and variants thereof capable of producing an alkaline cellulase K, and having the following enzymatic properties:
  (1) activity:
    having Cx enzymatic activity, weak $C_1$ enzymatic activity and a weak beta-glucosidase activity;
  (2) substrate specificity:
    acting on carboxymethyl cellulose (CMC), crystalline cellulose, microcrystallline cellulose, cellobiose, and p-nitrophenyl cellobioside (PNPC);
  (3) working pH and optimum pH:
    having a working pH in the range of 4 to 12 and an optimum pH in the range of 9 to 10;
  (4) pH stability:
    being stable at a pH of 4.5 to 10.5 and 6.8 to 10 when allowed to stand at 40° C. for 10 minutes and 30 minutes, respectively;
  (5) working temperature range and optimum working temperature;
    working over a temperature range of from 10 to 65° C. with an optimum temperature at about 40° C.;
  (6) influence of chelating agents:
    having an activity not impeded by ethylenediamine tetraacetic acid, ethyleneglycol-bis-(beta-aminoethylether)-N,N,N',N''-tetraacetic acid, N,N-bis(carboxymethyl)glycine (nitrilotriacetic acid), sodium tripolyphosphoate and zeolite;
  (7) influence of surface active agents:
    losing little activity by sodium linear alkylbenzenesulfonates, sodium alkylsulfates, sodium polyoxyethylene alkyl sulfates, sodium alpha-olefin sulfonates, sodium alpha-sulfonated aliphatic acid esters, sodium alkyl sulfonates, polyoxyethylene secondary alkyl ethers, fatty acid salts (sodium salts), and dimethyldialkylammonium chloride;
  (8) resistance to proteinases:
    having a strong resistance to proteinases;
  (9) molecular weight as determined by gel chromatography;
    having a molecular weight of 180,000±10,000.

* * * * *